US00PP09342P

United States Patent [19]

Sakazaki et al.

[11] Patent Number: Plant 9,342

[45] Date of Patent: Oct. 24, 1995

[54] PETUNIA PLANT NAMED 'REVOLUTION VIOLET'

[75] Inventors: Ushio Sakazaki, Hikone; Yuji Tamura, Kofu; Hiroshi Hirabayashi, Yachiyo, all of Japan

[73] Assignees: Suntory Limited, Osaka; Keisei Rose Nurseries, Inc., Tokyo, both of Japan

[21] Appl. No.: 369,323

[22] Filed: Jan. 6, 1995

Related U.S. Application Data

[63] Continuation of Ser. No. 234,620, Apr. 28, 1994, abandoned, which is a continuation of Ser. No. 90,267, Jul. 13, 1993, abandoned.

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,879 | 9/1994 | Danziger | Plt./68.1 |

*Primary Examiner*—James R. Feyrer
*Attorney, Agent, or Firm*—Burns, Doane, Swecker & Mathis

[57] ABSTRACT

Disclosed herein is a decumbent type petunia plant having a long stem. The plant has abundant branching and a great profusion of blooms, and the whole bush remains in bloom for a long period of time. The flowers are single and small, and the petals have a vivid purple color. The plant is highly resistant to rain, drought, and heat.

4 Drawing Sheets

This application is a continuation of application Ser. No. 08/234,620, filed Apr. 28, 1994 (now abandoned), which is a continuation application of Ser. No. 08/090,267, filed Jul. 13, 1993 (now abandoned).

BACKGROUND OF THE INVENTION

The present invention relates to a new and distinct variety of one petunia plant from self-pollination of one petunia plant having rose color petals which was selected from a crossing 'Recoverer Blue' (♀) and a wild type of petunia plant (♂) native to Brazil. The 'Recoverer Blue' parent is available from Sakata Seed Corp. in Japan.

Petunia is a very popular plant and is used for flower bedding and potting in the summer season. There are only a few varieties of the petunia plant which do not have an upright growth habit and which have a high resistance to rain, heat, and drought. The petunia series "Revolution" which we patented which includes the plants 'Revolution Purplepink,' U.S. Plant Pat. No. 6,915; 'Revolution Brilliantpink,' U.S. Plant Pat. No. 6,914; and 'Revolution Brilliantpink-Mini', U.S. Plant Pat. No. 6,899, are petunia plants having decumbent growth of branches, with long stems, a lower, spreading habit, abundant branching and high resistance to heat, drought, and rain. However there are only a few varieties having a wide range of a flower color. Accordingly, this invention was aimed to obtaining a new variety having a purple color petal, together with features of said 'Revolution' series.

The new variety of petunia plant according to this invention originated from a self-pollination of one petunia plants which was selected from a crossing of 'Recoverer Blue' and a wild type of petunia native to Brazil, in spring, 1989 at the Plant Biotechnology Laboratory, Institute for Fundamental Research of SUNTORY Ltd., residing at 2913-1 Torihara, Hakushu-cho, Kitakoma-gun, Yamanashi-Ken, Japan. From this crossing 500 seedlings were obtained in 1989, from which 5 seedlings were selected, propagated by cutting, and then grown as a trial by flower bedding and potting from the spring of 1990. Only one of the 5 resulting plants was selected. The botanical characteristics of the finally-selected plant were then examined, using a similar variety, 'Revolution Brilliantpink-mini', for comparison, from the spring of 1990. As a result, it was concluded that this petunia plant is distinguishable from any other variety, whose existence is known to us, and this new variety of petunia plant was named 'Revolution Violet'.

In the following description, the color-coding is in accordance with the Horticultural Color Chart of The Royal Horticultural Society, London, England (R.H.S. Color Chart), and the Inter-Society Color Council-Nation Bureau of Standards Color Name (I.S.C.C.-N.B.S. Color Name). A color chart based on The Japan Color Standard for Horticultural Plant (J.H.S. Color Chart) is also added for reference.

'Recoverer Blue', used as the female grandparent in the obtaining of petunia plant having rose color petal, is one of the 'Recoverer Series' bred by the Sakata Seed Corp., Japan. The 'Recoverer Series' includes 'Recoverer Scarletred', 'Recoverer White', 'Recoverer Pink', and 'Recoverer Blue', and these plants are commonly characterized by a resistance to rain. The main botanical characteristics of 'Recoverer Blue' are as follows.

Plant:

*Growth habit.*—Upright.

*Plant height.*—30–40 cm.

*Spreading area of plant.*—25–35 cm in diameter.

*Blooming period.*—April to September the southern Kanto area, Japan.

Stems:

*Thickness.*—Main stem 4.0–6.0 mm; lateral stem 2.0–3.0 mm.

*Color.*—Brilliant yellow green (R.H.S. 145B, J.H.S. 3504–3503).

*Branching.*—Abundant.

*Pubescence.*—Medium.

*Length of internodes.*—2.0–3.0 cm before blooming; 2.0–4.0 cm during blooming.

Leaf:

*Phyllotaxis.*—Verticillate before blooming; opposite during blooming.

*Shape.*—Oval.

*Size (average).*—4.5–5.0 cm×2.0–3.0cm.
*Thickness.*—0.3–0.5 mm.
*Color.*—Moderate olive green to moderate yellow green (R.H.S. 146A–137C, J.H.S. 3508–3712).
*Pubescence.*—Medium.

Flower: Opening obliquely upward.
*Type.*—Single.
*Shape.*—Funnel-shape, with corolla with five fused segments or petals; the petals having a conspicously dark midrib and veining and the corolla having a dark eye.
*Diameter.*—8.0–8.5 cm.
*Color.*—In the unopened stage (bud), dark reddish purple to black (R.H.S. 79A–202A, J.H.S. 8618—05; both when open and at full bloom, deep purple (R.H.S. 83A, J.H.S. 8606–8609).
*Reproductive organs.*—1 normal pistil having a strong yellow green (R.H.S. 143A, J.H.S. 3711) stigma, and 5 normal stamens each having a medium gray (R.H.S. 202B–202C, J.H.S.–0302) anther and a light purple (R.H.S. 87B–87C, J.H.S. 8304) filament.
*Peduncle.*—1.5–2.5 mm in thickness, and 2.5–3.0 cm in length.

Physiological and ecological characteristics: Resistance to rain, heat, and disease, and moderate resistance to pests.

The male grandparent used in the obtaining of petunia plant having rose color petal, is a wild type of petunia native to Brazil, the seeds of which were gathered at Gramado, Rio Grande Do Sul, Brazil and introduced to Japane in October, 1983. This wild type of plant is presently maintained at the aforementioned Plant Biotechnology Laboratory of Suntory Ltd. The main botanical characteristics of this male parent are as follows.

Plant:
*Growth habit.*—Decumbent.
*Plant height.*—20 cm.
*Spreading area of plant.*—100–150 cm in
*Blooming period.*—May to August in the southern Kantō area, Japan.

Stem:
*Length from base.*—50–80 cm.
*Thickness.*—Main stem 2.0–3.0 mm; lateral stems 1.5–2.5 mm.
*Color.*—Strong yellow green (R.H.S. 144B–144C, J.H.S. 3512–3513).
*Branching.*—Over-abundant.
*Pubescence.*—Heavy.
*Length of internodes.*—1.0–2.0 cm before blooming; 1.5–3.0 cm during blooming.

Leaf:
*Phyllotaxis.*—Opposite both before and during blooming.
*Shape.*—Oval.
*Size (average).*—4.5–5.5 cm×2.5–3.5cm.
*Thickness.*—0.4–0.5 mm.
*Color.*—Grayish olive green (R.H.S. 137A–137B, J.H.S. 3716–3717).
*Pubescence.*—Scant.

Flower: Opening obliquely upward.
*Type.*—Single.
*Shape.*—Funnel-shape, with corolla with five fused segments or petals.
*Diameter.*—4.0–5.0 cm.
*Color.*—In the unopened stage (bud), dark reddish purple (R.H.S. 79B, J.H.S. 8907–8909); when open, vivid reddish purple (R.H.S. 74A, J.H.S. 9207); at full bloom, vivid reddish purple (R.H.S. 80A, J.H.S. 8906).
*Reproductive organs.*—1 pistil and 5 stamens, both normal.
*Peduncle.*—0.9–1.2 mm in thickness, and 2.0–2.5 cm in length.

Physiological and ecological characteristics: High resistance to drought, relatively high resistance to heat, and moderate resistance to diseases and pests.

This new and distinct variety of petunia plant, 'Revolution Violet', was asexually reproduced by cuttings at the aforementioned Yachiyo Farms of Keisei Rose Nurseries, Inc., and Plant Biotechnology Laboratory, Institute for Fundamentals research of Suntory Ltd., and the homogeneity and stability thereof were confirmed.

SUMMARY OF THE VARIETY

The new variety of petunia plant has a decumbent habit and long stems, and thus is very different from similar variety, 'Recoverer Blue' having an upright growth habit. The plant has abundant branching and great profusion of blooms, and the whole bush remains in bloom for a considerable period of time, longer than the bloom period of 'Recoverer Blue'. The flowers are single and small, and smaller than 'Recoverer Blue', and the petals have a moderate purple color, with dark reddish purple lines radiating from a dark reddish purple center portion. The reverse side of the petal have a purple color. The plant is highly resistant to rain, heat, and drought.

DESCRIPTION OF THE VARIETY

Figure 1:
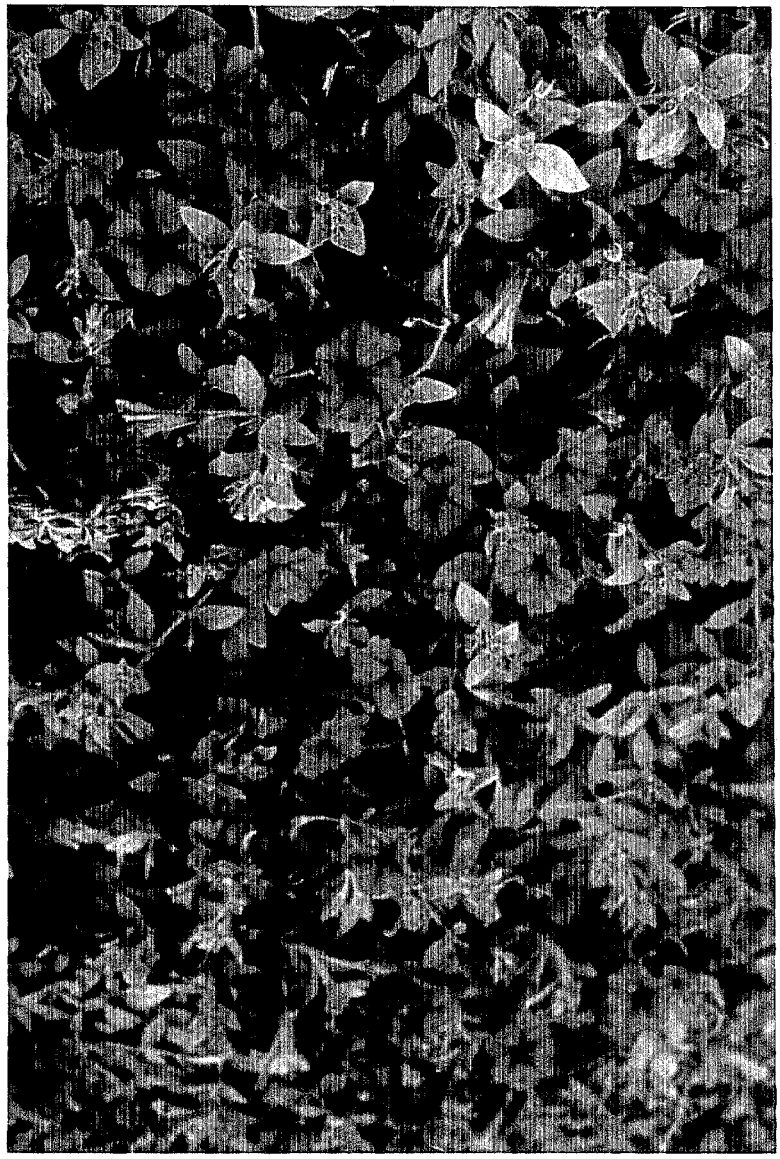
FIG. 1 is a photograph giving a partial view of the new variety of petunia plant planted in a flower bed.
Figure 2:
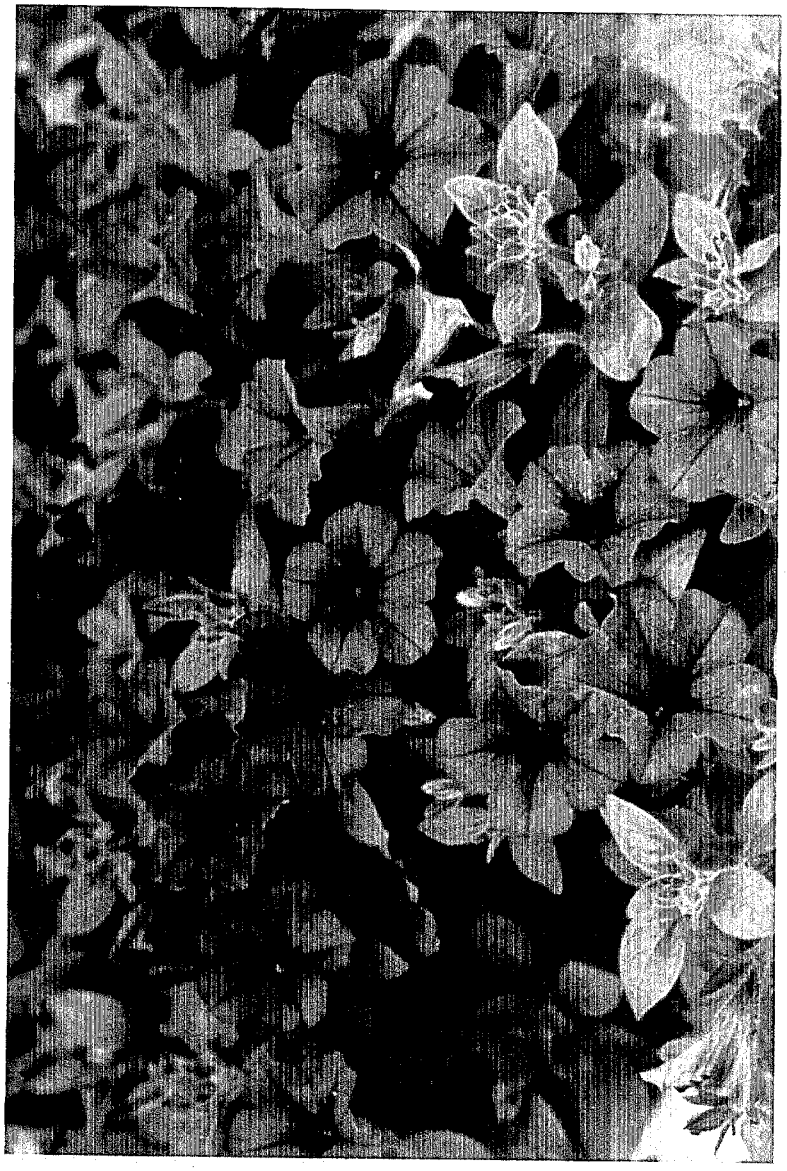
FIG. 2 is a photograph of flowers of the new variety of petunia plant.
Figure 3:
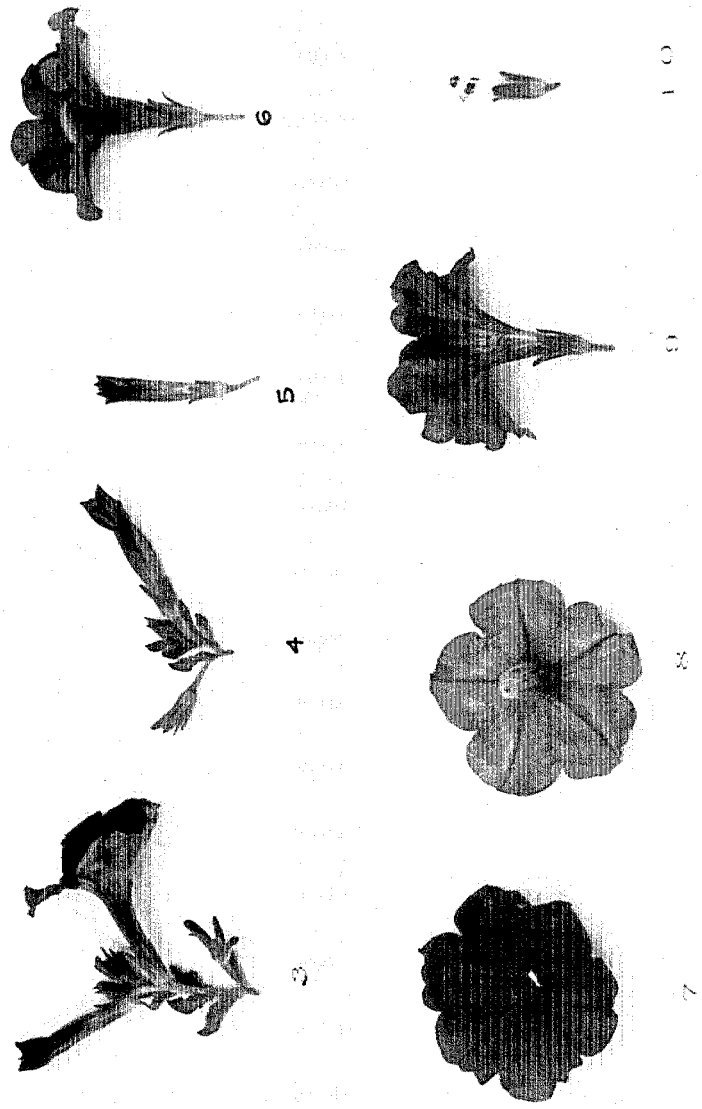
FIG. 3 is a photograph showing, in numerical order, a branch having an open flower (3), a current shoot (4), a bud (5), a side view of the flower (6), a front view of the flower (7), a rear view of the flower (8), an interior view of the flower (9), and the pistil and stamens (10), of the new variety of petunia plant.
Figure 4:
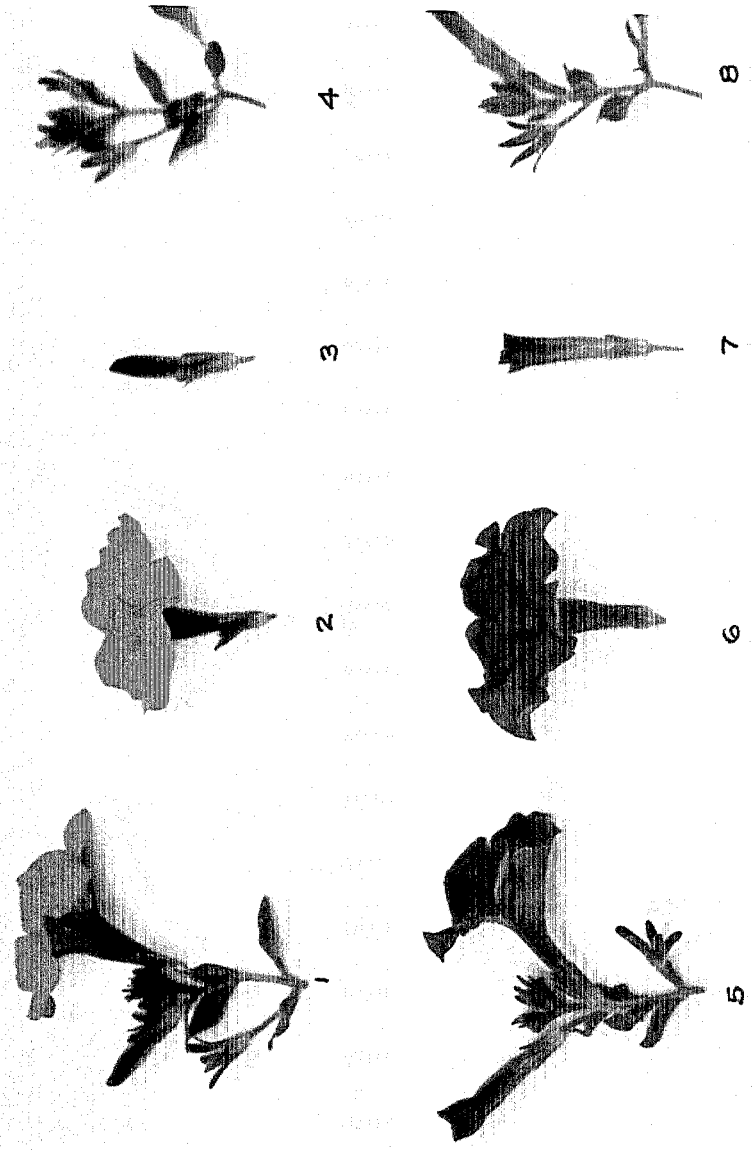
FIG. 4 is a photograph showing, in numerical order, a brunch having an open flower (1), a flower (2), a bud (3), and a current shoot (4) of a similar variety 'Revolution Brilliant-pink-mini', in comparison with corresponding items (5–8) of the new variety of petunia plant.

The botanical characteristics of the new and distinct variety of petunia plant, 'Revolution Violet' are as follows.

Plant:
*Growth habit.*—Decumbent. The stems hang down when potted in a hanging pot.
*Plant height.*—20–25 cm.
*Spreading area of plant.*—The stem extends to a length of 30–50 cm from the base, and thus the spreading area of the plant is 60–100 cm in diameter.
*Growth.*—Very vigorous with abundant branching, a great profusion of blooms; the whole bush remaining in bloom for a considerable period of time.
*Blooming period.*—Late March to Late September, in all areas of Japan. The plant shape does not change throughout this period.

Stems: Extending to 30–50 cm.
*Thickness.*—2.5–3.5 mm.

*Anthocyanin pigmentation.*—Absent.

*Pubescence.*—Medium.

*Branching.*—Over-abundant (primary), abundant (secondary).

*Length of internode.*—4.0–6.0 cm.

Leaf:

*Leaf attaching angle to stem.*—Horizontal.

*Shape.*—Oval.

*Length.*—3.0–6.0 cm.

*Width.*—1.5–3.5 cm.

*Thickness.*—0.6–0.8 cm.

*Color.*—Strong yellow green (R.H.S. 144A, J.H.S. 3707).

*Pubescence.*—Medium.

Flower: Opening obliquely upward.

*Type.*—Single.

*Shape.*—Funnel-shape, with corolla with five fused segments or petals.

*Diameter.*—4.0–5.0 cm.

*Petal color.*—Vivid purple (R.H.S. 88A, J.H.S. 8306); petal bottom color of inside surface of throat is light purple (R.H.S. 76A, J.H.S. 8603). The reverse of the petal is strong purple (R.H.S. 83D, J.H.S. 8612).

*Reproductive organs.*—1 normal pistil and 5 normal stamens (2 stamens are higher than pistil). Pistil is normal and generally typical of the species shape and stamens are medium shape. The new variety is both male and female fertile.

*Peduncle.*—2.5 mm in thick, and 0.1 cm in length.

*Ploidy.*—The new variety is believed to be diploid consistent with the diploid character of its parents.

Physiological and ecological characteristics: High resistance to drought, rain, and heat. Also high resistance to diseases. Moderate resistance to pests.

This new variety of petunia plant is most suitable for flower bedding and potting, particularly in hanging pots or planters, and further excellent for ground cover. When good soil conditions are present with adequate moisture, the new variety spreads by the rooting of the nodes of stems.

The plant of this new variety 'Revolution Violet' is presently planted and maintained at the Plant Biotechnology Laboratory, Institute for fundamental Research of Suntory Ltd., residing at 2913-1 Torihara, Hakushu-cho, Kitakoma-gun, Yamanhashi-ken, Japan.

We claim:

1. A new and distinct variety of petunia plant, substantially as herein illustrated and described, characterized particularly as to novelty by (A) being a decumbent habit plant having long stems, (B) an abundant branching and a great profusion of blooms, the whole bush remaining in bloom for a considerable period of time, (C) flowers that are single and small, the petals having a vivid purple color, and (D) a high resistance to rain, drought, and heat.

* * * * *